United States Patent [19]

Kirkham

[11] Patent Number: 4,634,856

[45] Date of Patent: Jan. 6, 1987

[54] FIBER OPTIC MOISTURE SENSOR WITH MOISTURE-ABSORBING REFLECTIVE TARGET

[75] Inventor: Randy R. Kirkham, Richland, Wash.

[73] Assignee: The United States of America as represented by the United States Department of Energy, Washington, D.C.

[21] Appl. No.: 637,627

[22] Filed: Aug. 3, 1984

[51] Int. Cl.[4] ............................................. H01J 5/16
[52] U.S. Cl. ..................................... 250/227; 250/557
[58] Field of Search ................... 250/227, 577, 231 R; 73/293; 455/610, 612

[56] References Cited

U.S. PATENT DOCUMENTS 3,120,125  2/1964  Vasel ..................................... 250/577
4,270,049  5/1981  Tanaka et al. ....................... 250/227
4,422,714  12/1983  Benoit et al. ......................... 250/577

Primary Examiner—David C. Nelms
Attorney, Agent, or Firm—Edward W. Nypaver; Robert Southworth, III; Judson R. Hightower

[57] ABSTRACT

A method and apparatus for sensing moisture changes by utilizing optical fiber technology. One embodiment uses a reflective target at the end of an optical fiber. The reflectance of the target varies with its moisture content and can be detected by a remote unit at the opposite end of the fiber. A second embodiment utilizes changes in light loss along the fiber length. This can be attributed to changes in reflectance of cladding material as a function of its moisture content. It can also be affected by holes or inserts interposed in the cladding material and/or fiber. Changing light levels can also be coupled from one fiber to another in an assembly of fibers as a function of varying moisture content in their overlapping lengths of cladding material.

2 Claims, 4 Drawing Figures

FIBER OPTIC MOISTURE SENSOR WITH MOISTURE-ABSORBING REFLECTIVE TARGET

The United States Government has rights in this invention pursuant to Contract DE-AC06-76RLO 1830 between the U.S. Department of Energy and Battelle-Northwest Laboratories.

BACKGROUND OF THE INVENTION

This disclosure relates to monitoring of environmental moisture changes in areas such as the surfaces of liquid tanks or in irrigated soil. It uses fiber optical technology for sensing moisture conditions.

Fiber optic research and implementation has branched out from applications in data communication fields into environmental monitoring applications where the optical fibers are used as sensing elements. Temperature, pressure and strain gauges made from optical fibers are currently being evaluated by various research groups. Most of these sensing elements rely upon an environmental parameter, such as temperature, pressure, or strain, to induce a change in the refractive index of either the cladding or fiber material.

This disclosure has been prompted by a research effort to apply fiber optic technology to the sensing of moisture conditions. It is capable of a wide variety of practical applications. One example might be detection of moisture changes on the surfaces of waste tanks surrounding radioactive waste storage facilities to detect liquid leakage. Agricultural applications for monitoring of irrigation practices are also feasible.

SUMMARY OF THE INVENTION

It is one object of the invention to provide a new and useful method and sensing apparatus for monitoring environmental moisture conditions and changes.

Another object of this invention is to provide a moisture sensing apparatus that can be remotely connected to expensive and sensitive electronic monitoring equipment. This equipment can be safely enclosed within an indoor area not exposed to the moisture conditions being monitored.

To achieve the foregoing and other objects, and in accordance with the purposes of the present invention as embodied and broadly described herein, the method of this invention may comprise the steps of locating a moisture-sensitive optical fiber assembly within the environmental area being monitored, the transmission of light signals through the fiber assembly, and the detecting of changes in the light signals as an indication of the moisture conditions to which the fiber assembly has been subjected.

The apparatus for monitoring environmental moisture changes comprises a moisture sensitive optical fiber assembly located within the monitored area, a light source, and detection means for measuring changes in light signals transmitted through the optical fiber assembly from the light source as an indication of the environmental moisture conditions to which the optical fiber assembly is subjected.

DESCRIPTION OF THE PREFERRED EMBODIMENTS

This disclosure describes a method and apparatus for monitoring environmental moisture changes at surfaces or areas where moisture conditions are critical. Specific application examples might include the monitoring of leakage along surfaces of liquid storage tanks, or the monitoring of soil moisture conditions in irrigated fields.

Two basic forms of the invention are described. The first system (FIG. 1) utilizes changes in reflectance of target materials used in conjunction with an optical fiber assembly. The second system (FIGS. 2, 3, and 4) uses changes in the refractive index of the optical fiber cladding. Common to both systems is the utilization of material property changes in the optical fiber assembly as a function of moisture content.

In the first system, the optical fiber transmits light to and from the sensing target element. The amount of light return for detection purposes is a function of the reflectance at the target. By selecting a target material having a reflectance that varies with its moisture content, the reflected light will provide a signal corresponding to moisture content changes over a period of time during which the signal is monitored.

The second system utilizes changes in the refractive index of the optical fiber cladding material as the moisture sensor. The cladding must be selected from among materials having a variable refractive index that is a function of its moisture content. Other approaches in this system might use induced fiber imperfections, such as splices or microscopic holes in the fiber created by lasers, which will have different optical qualities depending upon their moisture content. Two or more fibers might also be used as a couple, with the amount of light coupled from one fiber to another being a function of the moisture content of their cladding materials.

Techniques by which the optical fiber assemblies can be used as moisture sensors are discussed below.

Reflectance measurement is a standard technique used with optical fibers for detection of changes in the distance separating a reflective surface from the monitored end of the optical fiber. By using a reflective target material having reflective qualities which vary with moisture content, measurement of reflectance can be used to provide an indication of moisture content changes.

Figure 1:
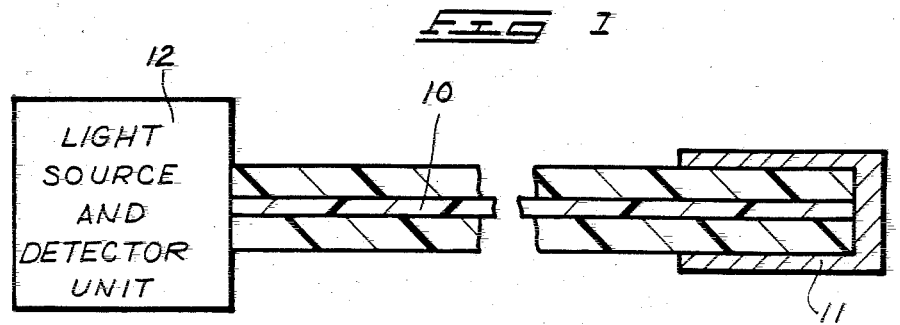
FIG. 1 is a schematic sectional view showing a first form of the apparatus.

This first system is schematically illustrated in FIG. 1, where an optical fiber 10 has a reflective target 11 at one end and a conventional light source and reflectance monitor 12 at its remaining end. Since the target 11 is stationary relative to the optical fiber 10, measured changes in reflectance will be a direct function of moisture changes. The material comprising the target 11 must have reflective properties which vary with changes in moisture content.

Examples of materials suitable for use as the operative element in target 11 are porous ceramic. A suitable unit serving as the light source and detector unit 12 is a light emitting diode for illumination and a photosensitive diode coupled with an operational amplifier for detection.

This system is capable of providing very accurate moisture measurement in surface soils for research measurement purposes. Because a small physical target can be used, the danger of damage to the sensor is relatively slight. The system can be designed so as to be durable in exterior applications.

The light transmitting efficiency of optical fiber assemblies is partially the result of the refractive index of the fiber itself, and partly the result of the refractive index of the cladding material surrounding the fiber. This cladding material can be air, glass, plastic resin, or in the present instance, water or water content within the cladding material. The more water that is present, the larger the reduction in signal transmittance that will be encountered. Light will be coupled out of the optical fiber as the cladding material develops a refractive index closer to the refractive index of the optical fiber. This sensitivity to moisture permits use of the optical fiber elements as moisture detectors for industrial and agricultural purposes.

Figure 2:
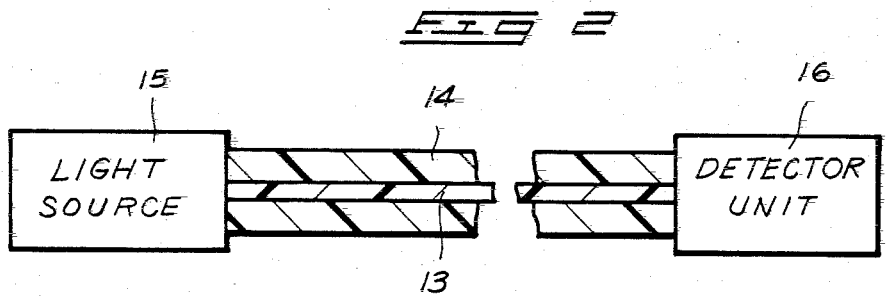
FIG. 2 is a schematic sectional view showing a second form.

FIG. 2 illustrates a practical arrangement for utilizing such properties in moisture detection system. It shows an optical fiber 13 surrounded by cladding material 14 having a refractive index which is a function of its moisture content. Examples of such materials are sintered or porous plastic. The strength of light signals transmitted between a light source 15 at one end of the fiber 13 and a detector unit 16 at its opposite end will vary as a function of the moisture content within the cladding material 14.

Figure 3:
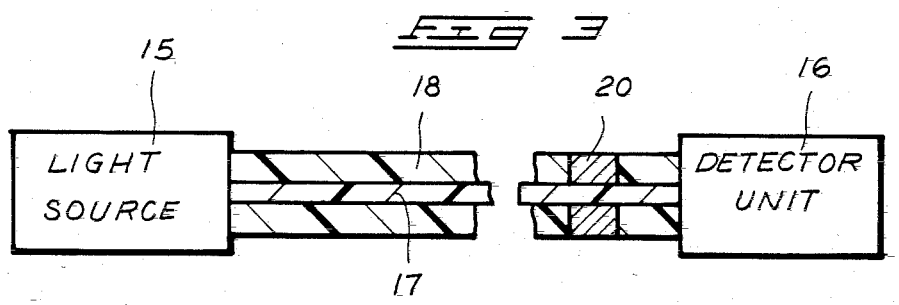
FIG. 3 is a schematic sectional view showing a third form.

FIG. 3 shows a variation wherein an optical fiber 17 is surrounded by conventional cladding material 18 having one or more insertions 20 of a material whose light conductance properties changes with moisture content. An example of such materials is a porous ceramic collar surrounding the optical fiber 17 and inserted within the length of cladding material 18. Cladding material modifications might also be accomplished by forming controlled apertures through the cladding material and/or optical fiber by laser energy. Such apertures would fill with water as a function of the aperture diameter and moisture availability. The resulting changes in light conductance through the optical fiber 17 provides a direct indication of moisture content in the area of the fiber modification.

Figure 4:
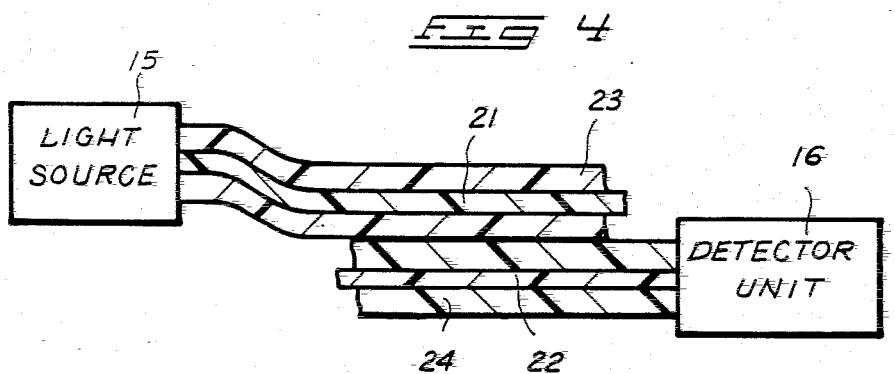
FIG. 4 is a schematic sectional view showing a fourth form.

A third illustration of a system having light loss properties that vary with moisture content is shown in FIG. 4. Two or more optical fibers 21 and 22 have at least a portion of their cladding 23 and 24 closely adjacent or contacting one another. The cladding material used in this instance must have the property of varying light reflectance as a function of its moisture content. Light will be coupled out of one fiber and into the other as a function of the water content of the cladding material.

The detector unit 16 schematically shown in FIGS. 2, 3, and 4 can be a conventional optical time-domain reflectometer which provides information on optical fiber signal loss throughout the length of the fiber. An example of an optical time-domain reflectometer which could be used in such a system is Tetronix Model OF150 Optical Time Domain Reflectometer. Such equipment can be used to measure moisture content at any point along the entire length of an elongated optical fiber arranged about or along a substantial area being monitored. An example would be a long optical fiber wrapped around a waste storage tank. In this systems, moisture measurements can be made at many points along a single optical fiber cable containing numerous individual optical fibers for monitoring at the desired locations. The cable can be buried in soil or beneath a pond liner containing liquid being monitored.

The foregoing description of the preferred embodiments of this invention has been presented for purposes of illustration and description. It is not intended to be exhaustive or to limit the invention to the precise steps disclosed. Obviously, many modifications and variations are possible in view of the above teaching. The embodiment of the method and apparatus was chosen and described in order to best explain the principles of the invention and its practical application as to enable others skilled in this art to best utilize the invention. It is contemplated that various embodiments and modifications suited to a particular use will utilized. It is intended that the scope of the invention be defined by the claims attached to this disclosure.

I claim:

1. A method for monitoring environmental moisture changes, comprising the following steps:
    locating a optical fiber assembly within the environmental area being monitored;
    transmitting light signals through the optical fiber assembly from a light source to and from a target whose reflectance is a function of the target's moisture content;
    measuring the returned light reflected by the target;
    and detecting changes in the light signals transmitted through the optical fiber assembly from the light source as an indication of the moisture conditions to which the optical fiber assembly is subjected.

2. An apparatus for monitoring environmental moisture, comprising:
    a optical fiber assembly located within the environmental area being monitored;
    a light source for directing light signals through the optical fiber assembly;
    a moisture-sensitive reflective target at an end of at least one optical fiber within the optical fiber assembly and exposed to said light source;
    and detection means for measuring changes in the reflectance of said target as an indication of the environmental moisture conditions to which the target is subjected.

* * * * *